United States Patent
Dias (10) Patent No.: US 9,403,509 B2
(45) Date of Patent: Aug. 2, 2016

(54) METHOD AND DEVICE TO CONTROL POWER CONSUMPTION IN A WINDSHIELD WIPER UNIT

(75) Inventor: Dominique Dias, St. Remy les chevreuses (FR)

(73) Assignee: Valeo Systèmes d'Essuyage, Le Mesnil Saint Denis (FR)

( * ) Notice: Subject to any disclaimer, the term of this patent is extended or adjusted under 35 U.S.C. 154(b) by 227 days.

(21) Appl. No.: 14/118,681

(22) PCT Filed: Apr. 26, 2012

(86) PCT No.: PCT/EP2012/057589
§ 371 (c)(1),
(2), (4) Date: Nov. 19, 2013

(87) PCT Pub. No.: WO2012/159844
PCT Pub. Date: Nov. 29, 2012

(65) Prior Publication Data
US 2014/0082874 A1 Mar. 27, 2014

(30) Foreign Application Priority Data
May 20, 2011 (EP) .................................... 11305619

(51) Int. Cl.
*H02P 3/02* (2006.01)
*G01N 19/02* (2006.01)
(Continued)

(52) U.S. Cl.
CPC ............. *B60S 1/0818* (2013.01); *B60S 1/0859* (2013.01); *G01M 5/0033* (2013.01); *G01N 19/02* (2013.01); *H02P 3/02* (2013.01)

(58) Field of Classification Search
USPC ................................ 318/476, 432; 15/250.12
See application file for complete search history.

(56) References Cited

U.S. PATENT DOCUMENTS 5,568,026 A * 10/1996 Welch ................... B60S 1/0814
318/41
6,703,804 B1 * 3/2004 Courdier ................... B60S 1/08
318/280

(Continued)

FOREIGN PATENT DOCUMENTS

DE 25 04 799 A1 8/1976
EP 1 010 594 A1 6/2000
(Continued)

OTHER PUBLICATIONS

International Search Report for corresponding International Application No. PCT/EP2012/057589, mailed Jun. 14, 2012 (2 pages).

*Primary Examiner* — Paul Ip
*Assistant Examiner* — Said Bouziane
(74) *Attorney, Agent, or Firm* — Osha Liang LLP (57) ABSTRACT

This invention concerns a method to detect the wetness state of a vehicle windshield surface (S) comprising a windshield wiper unit (1), the windshield wiper unit (1) comprising: —wiper blades (5) configured to wipe the windshield surface (S) when set in motion, —at least one motor (7) configured to set the wiper blades (5) in motion, —a controller (9), configured to control the at least one motor (7), the method comprising the steps: —measuring the power consumption of the at least one motor (7), —determining the wiping speed (W) of the wiper blades (5), —using the measured power consumption and determined wiping speed (W) to deduce a friction related coefficient of the windshield surface (S), —comparing the deduced value to at least one predetermined value in order to determine the wetness state of the vehicle windshield surface (S).

9 Claims, 4 Drawing Sheets (51) Int. Cl.
  *B60S 1/08* (2006.01)
  *G01M 5/00* (2006.01)

(56) References Cited

U.S. PATENT DOCUMENTS

2003/0087767 A1* 5/2003 Goto .................. B60S 1/38
                                                          508/113

2008/0016644 A1* 1/2008 Mizote .................. B60S 1/38
                                                          15/250.361
2008/0060677 A1* 3/2008 Nakano .................. B60S 1/486
                                                          134/6

FOREIGN PATENT DOCUMENTS

FR    2 528 777 A1   12/1983
FR    2 785 246 A1    5/2000

* cited by examiner

METHOD AND DEVICE TO CONTROL POWER CONSUMPTION IN A WINDSHIELD WIPER UNIT

The invention relates to a method and device to control power in a windshield wiper unit.

To develop electrical vehicles with a larger autonomy, two aspects are relevant. On one hand the maximum battery load, and on the other hand the average power consumption of the vehicle.

In a normal vehicle the electrical consumption of the peripheral circuits such as radio, indoor ambiance or pictogram lights and windshield wiper unit is only moderately relevant since the running engine reloads the battery through an alternator. On the opposite, for the electrical vehicle, the slightest consumption reduction means more autonomy at same battery status.

The windscreen wiper units in use involve a plurality of electrical motors, setting wiper blades in motion when powered with current. When set in motion, the wiper blades wipe the surface of the windshield, in order to clean it from water and other fluids lowering the driver's vision.

On a dry windshield surface, the friction forces are more important. This leads to either lowering the wiping speed or increasing the power consumption, and faster blade wearing off. It is therefore known to use a water droplet or water film detector, often based on an optical sensor, which is placed somewhere on the windshield surface.

These windshield water detectors use only a surface of a few square centimeters as a representative sample, which can lead to false wetness state interpretation.

In order to overcome at least partially the aforementioned drawbacks, the invention has for object a method to detect the wetness state of a vehicle windshield surface comprising a windshield wiper unit, the windshield wiper unit comprising:
- wiper blades configured to wipe the windshield surface when set in motion,
- at least one motor configured to set the wiper blades in motion,
- a controller, configured to control the at least one motor, the method comprising the steps:
- measuring the power consumption of the at least one motor,
- determining the wiping speed of the wiper blades,
- using the measured power consumption and determined wiping speed to deduce a friction related coefficient of the windshield surface,
- comparing the deduced value to at least one predetermined value in order to determine the wetness state of the vehicle windshield surface.

This method allows to determine the wetness state of the windshield surface to avoid unnecessary wiping of the dry surface, said wiping of dry surface implying useless power consumption and blade wearing.

The method may have one of the following characteristics.

The controller stores and compares the friction related coefficient values over a predetermined amount of time, and uses lowest friction related coefficient values for wet state reference values, and highest friction related coefficient values for dry state reference values.

The controller is connected to a windshield washing unit, and the predetermined value is determined using a calibration, the calibration comprising the steps:
- wetting the windshield surface by activating the windshield washing unit,
- measuring the power consumption of the at least one motor,
- determining the wiping speed of the wiper blades,
- using the measured power consumption and wiping speed to deduce a reference friction related coefficient of the wet windshield surface,
- using said wet windshield surface reference friction related coefficient to establish the predetermined value.

Another object of the invention is a method to control power consumption in a windshield wiper unit, the windshield wiper unit comprising:
- wiper blades configured to wipe the windshield surface when set in motion,
- at least one motor configured to set the wiper blades in motion,
- a controller, configured to control the at least one motor, characterized in that the method comprises the steps:
- determining the wetness state of the windshield surface using the above mentioned method,
- if the determined wetness state is dry, the controller stops motion of blades.

Also, the invention relates a method to control power consumption in a windshield wiper unit, the windshield wiper unit comprising:
- wiper blades configured to wipe the windshield surface when set in motion,
- at least one motor configured to set the wiper blades in motion,
- a controller, configured to control the at least one motor, characterized in that the method comprises the steps:
- the controller receives a stop instruction, destined to trigger a stop of motion of blades,
- detecting the wetness state of the windshield surface using the above mentioned method,
- if the detected wetness state is wet, the controller maintains motion of blades.

The method may comprise one of the following characteristics, taken separately or in combination.

The steps of detecting the wetness state and of maintaining the wiping motion are repeated in a loop until detected wetness state is dry, the controller then stopping motion of blades.

Also the invention relates to a method to detect the weariness state of wiper blades of a vehicle windshield wiper unit, the windshield wiper unit comprising:
- at least one motor configured to set the wiper blades in motion,
- a controller, configured to control the at least one motor, characterized in that it comprises the steps:
- measuring the power consumption of the at least one motor,
- determining the wiping speed of the wiper blades,
- using the measured power consumption and determined wiping speed to deduce a friction related coefficient of the windshield surface,
- comparing the deduced value to at least one predetermined value in order to determine the weariness state of wiper blades of the vehicle windshield wiper unit.

The method may comprise one or more of the following characteristics.

The controller compares over time the highest registered friction related coefficient values, and detects a rise in said maximum values in order to determine the weariness state of wiper blades of the vehicle windshield wiper unit.

The predetermined value is determined using a calibration, the calibration comprising the steps:
- measuring the power consumption of the at least one motor (7) on dry windshield surface,
- determining the wiping speed of the wiper blades on dry windshield surface, using the measured power consumption and determined wiping speed to deduce a reference friction related coefficient of the dry windshield surface, setting the predetermined value to at least 150% of said wet windshield surface reference friction related coefficient value.

The invention also relates to the associated windshield wiper unit comprising:

wiper blades configured to wipe the windshield surface when set in motion, at least one motor configured to set the wiper blades in motion, a controller, configured to control the at least one motor, characterized in that the controller comprises:

means to measure the power consumption of the at least one motor, means to determine the wiping speed of the wiper blades, and in that the controller is configured to:

use the measured power consumption and determined wiping speed to deduce a friction related coefficient of the windshield surface, compare the deduced value to at least one predetermined value in order to determine the wetness state of the vehicle windshield surface.

The controller may be further configured to stop the wiping motion of the blades if the determined wetness state is dry.

Finally, the invention relates to the windshield wiper unit comprising:

wiper blades configured to wipe the windshield surface when set in motion, at least one motor configured to set the wiper blades in motion, a controller, configured to control the at least one motor, characterized in that the controller comprises:

means to measure the power consumption of the at least one motor, means to determine the wiping speed of the wiper blades, and in that the controller is configured to:

determine the wetness state of windshield surface using the method according to any of the precedent claims, use the measured power consumption and determined wiping speed to deduce a friction related coefficient of the windshield surface, if windshield surface is dry, compare the deduced friction related coefficient value on dry windshield surface to at least one second predetermined value in order to determine the weariness state of wiper blades of the vehicle windshield wiper unit.

Other characteristics and advantages will appear at the reading of the following description of the accompanying figures, among which.

Figure 1:
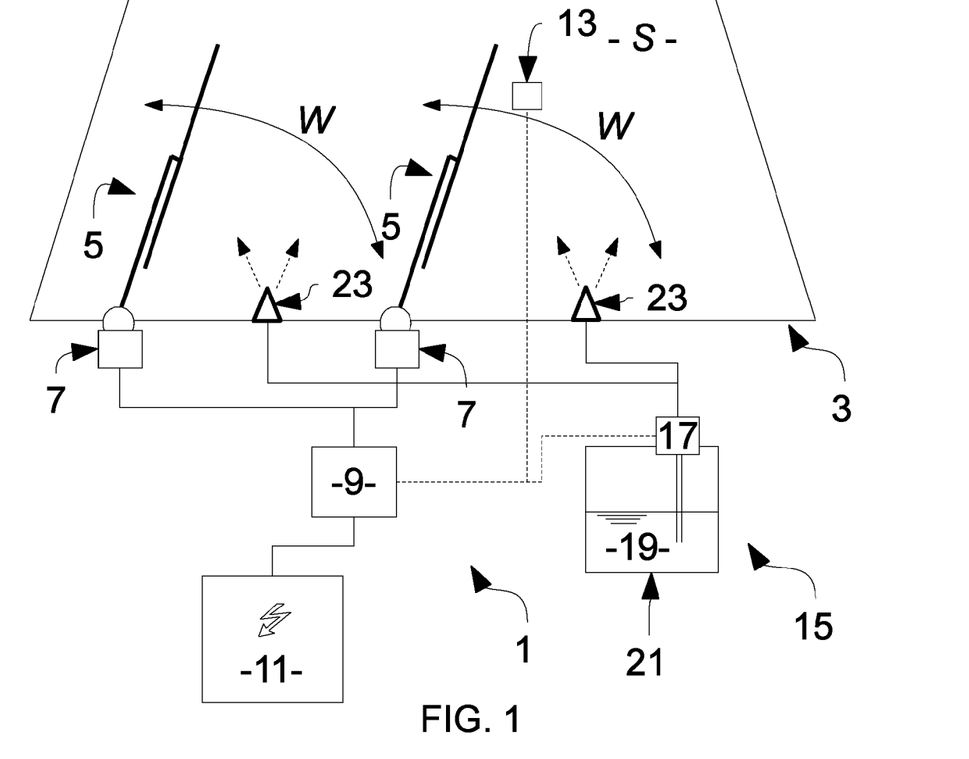
FIG. 1 is a schematic view of a windshield wiping unit.

The invention relates to a vehicle windshield wiper unit, and more particularly to a method to manage power consumption in such a windshield wiper unit. FIG. 1 represents schematically a windshield and the associated windshield wiper unit 1.

The windshield 3 comprises an external surface S which receives rain or other stain from the surroundings when the vehicle is driven. On said surface S are placed windshield wiper blades 5. The blades 5 are connected to respective motors 7, the motors 7 are able to set the blades 5 in motion by applying a torque at the base of the blades 5. Said motors 7 are fed with electrical power via a controller 9, configured to apply specific wiping programs by controlling the wiping speed W of blades 5. The power to run the motors 7 is delivered by the vehicle battery 11 or an alternator of the vehicle.

The controller 9 can also be connected to a droplet detector 13. The rain sensor 13 is usually an optical sensor placed on the surface S using infrared dispersion and reflection of infrared beams inside the windshield glass.

The windshield wiper unit 1 comprises blades 5, motors 7 and controller 9.

Also represented on FIG. 1 is a windshield washing unit 15. Said unit comprises a pump 17, connected to the controller 9, and configured to pump on driver request washing fluid 19 from a tank 21 to spraying nozzles 23. Said nozzles 23 direct a washing fluid spray on the windshield surface S to clear it from dust or stain.

The wiper unit 1 is usually controlled by the driver via a lever or any form of actuator in the passenger compartment, most often near the steering wheel, or on the dashboard, or automatically by the rain sensor 13. Several wiping speeds or programs are available: off, single wipe, intermittent INT, low speed LS and high speed HS. To supply the power delivered to motors 7, the controller 9 can use pulse width modulation on the current delivered to said motors 7.

According to the supplied current, the motor applies a torque to the blades 5 who are set in motion. The friction of the blades 5 on surface S produces a friction torque opposed to the motor applied torque.

The friction torque also greatly depends on the wetness state of the windshield surface S. In particular, it is significantly lower when surface S is wet. This is represented on FIG. 2, where the curves of the power consumption p of motors 7 as a function of wiping speed W with a wet windshield for curve $p_{wet}$ and a dry windshield for curve $p_{dry}$ are pictured.

Figure 2:
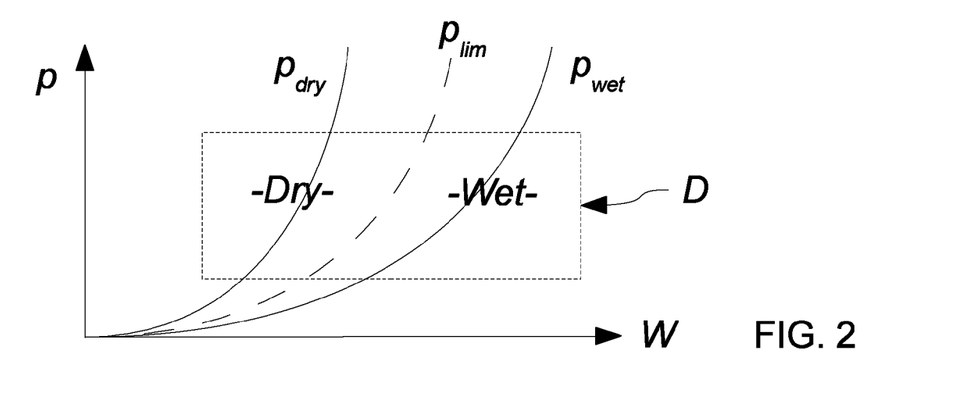
FIG. 2 is a simplified graph representing the power consumption as a function of the wiping speed in different windshield wetness states

The different operating modes restrain the functioning domain to domain D on FIG. 2, where the difference between wet and dry is easily done.

The power consumption p increases more than linearly with wiping speed W, roughly with square or cube of W depending on friction model. But at any W, $p_{wet}$ is smaller than $p_{dry}$. This allows to draw an intermediate curve $p_{lim}$. Underneath intermediate curve $p_{lim}$ the windshield is assumed wet, and above intermediate curve $p_{lim}$ the windshield is assumed dry.

The steepness of the power over speed curves p(W) depends on the friction coefficient, the friction related coefficient can be of the form $p(W) \cdot W^{-\beta}$, where $\beta$ is a positive coefficient depending on the model chosen to represent the dynamics. In particular, the choice of $\beta=0$ corresponds to a direct comparison of the power values.

Using the Coulomb law, a factor of four to five is measured between friction on dry surface and friction on wet surface. The difference is therefore easily noticeable. For example the usual friction coefficient values on wet surface are around 0.2 or 0.3, whereas on dry surface, the value is above 0.8.

The controller 9 comprises means to measure the power consumption of the motors 7. For example, said consumption measuring means can comprise a current estimator measuring the current delivered to the motor, and an integrator to obtain a mean current value over one, preferably few cycles. Measuring the power consumption will thus consist in letting the motors 7 run the predetermined number of wiping cycles, and determine the consumption p.

The controller also comprises means to determine the wiping speed of blades 5, for example by knowing the wiping speed W corresponding to the current wiping mode off, intermittent INT, low speed LS, or high speed HS.

In a first step, the power consumption of the motors 7 is measured. This allows to determine a power/speed p,W operating point for the wiper unit 1.

From the measured speed W and power consumption p a friction related coefficient is deduced that is compared to a predetermined value. The predetermined or threshold value can be equal to or slightly above a predetermined wet-state friction coefficient value, stored in memory. Said value can be either given by the manufacturer, or elaborated using a calibration.

This allows to deduce the wetness state of windshield surface S.

As an example, the measured power consumption can compared to the limit power value at measured speed W, $p_{lim}(W)$. By comparing the measured power to $p_{lim}(W)$, the method places the operating point p,W on the graph of FIG. 2.

Figure 3:
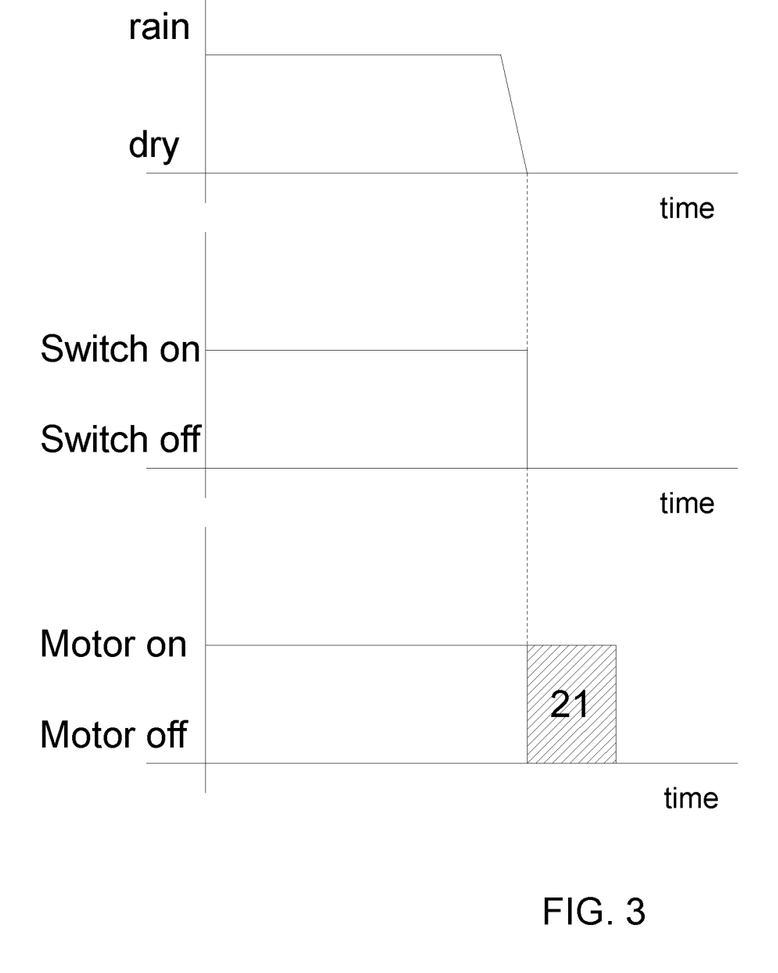
FIG. 3 is a schematic representation of the steps of one embodiment of a method according to the invention.
Figure 4:
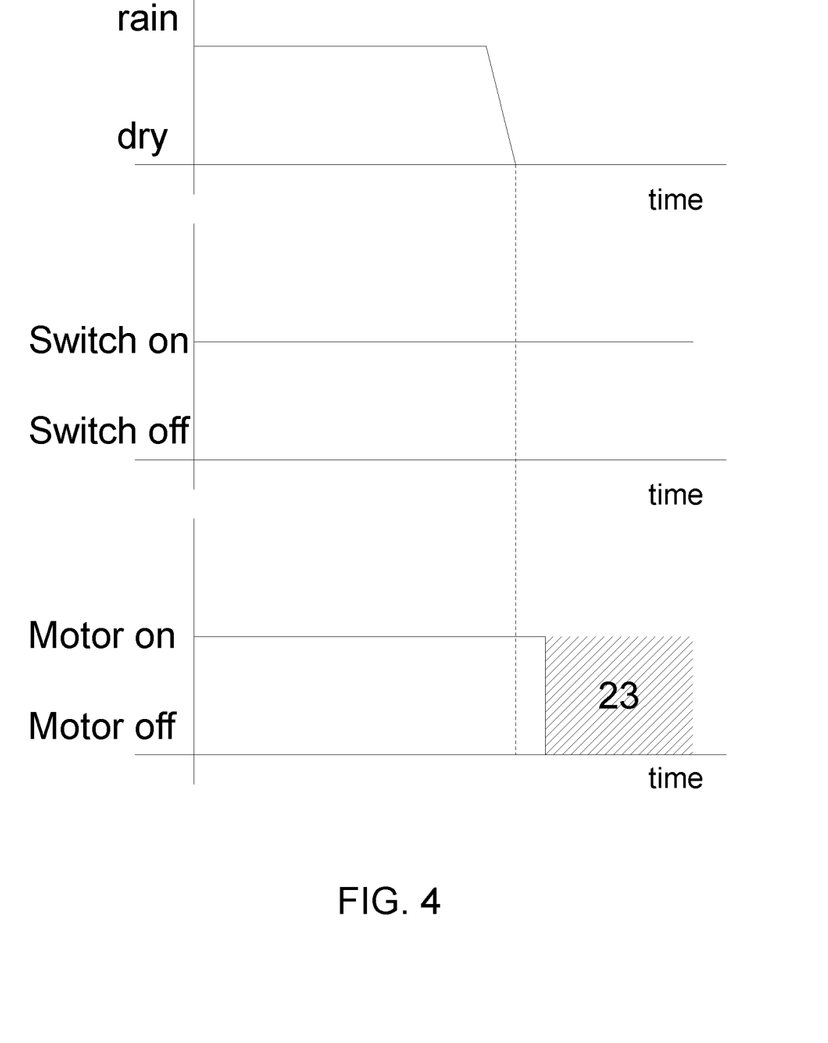
FIG. 4 is a schematic representation of the steps of a second embodiment of a method according to the invention.

FIGS. 3 and 4 picture scenarios in which the wetness state detection as described intervenes to avoid unnecessary power consumption and blade 5 wearing wiping of surface S in dry state.

The FIGS. 3 and 4 show along time the state of the rain condition (rain or dry), the wipe switch condition (switch on or switch off) and the wiper motor 7 condition (motor on or motor off).

In FIG. 3, the scenario is the following: the user has switched on the wiper motor 7 because rain is falling. After a time it stops raining, so the user puts the switch back to off position.

Alternatively, the start and stop wiping instructions may have been emitted by the rain sensor 13 if equipped.

Since residual water remains on windshield surface S, the friction coefficient remains low, the controller 9 still detects the surface S being wet, and therefore continues the wiping even though a stop instruction has been received. After a certain wiping time, surface S is dry, the friction increases, and the controller 9 detecting the increased friction stops the wiping. During the time between switching off and the moment where motors 7 stop, interval highlighted and marked 21 on FIG. 3, the wiper unit 1 cleans the surface S despite stop instruction, ensuring total dryness of the surface S.

In the case where the vehicle is equipped with a rain sensor 13 who initiates and stops the wiping motion upon detection of rain and detection of absence of rain, it is possible that said sensor does not detect water still present on windshield surface S. This happens noticeably when water flows for example from the roof in shallow streams, who might be running around the very localized sensor 13. This case is solved by the invention as explained above.

Also, the stop instruction can be sent by a windshield washing unit 15 if equipped, a predetermined number, one for example, of wiping cycles after spraying a windshield washer fluid 19 on the windshield surface S. Compared to usual post spraying behavior, potentially less cleaning wiping cycles are performed, and it is ensured that the wiping only stops when the windshield surface S is clean and dry.

In FIG. 4, the scenario is the following: the user has switched on the wiper motor 7 because rain is falling. After a time it stops raining, but the user does not put the switch back to off position.

Without stop instruction, the controller 9 maintains the wiping motion, until the windshield surface S is dry. The controller 9 then detects the increased friction due to dry state of surface S, and consequently stops the wiping motion, despite the absence of stop instruction, be it from user or rain sensor 13.

The highlighted part 23 of time in FIG. 4 corresponds to the time where due to absence of stop instruction the wiping motion would have been maintained on dry surface S, meaning increased power consumption and useless wear of blades 5. This is avoided thanks to the invention as explained above To determine the threshold power or friction related coefficient value, the wiper unit may also perform a calibration. The calibration would be performed when changing the blades 5 or at initiation/reset of the vehicle electronics.

A calibration would comprise the steps of wetting the windshield surface S using windshield washer unit 15 if the vehicle is equipped, and running a certain number of cycles while measuring the power consumption to obtain a reference coefficient value from which the threshold value will be deduced, for example by setting it at at least 150% of said wet windshield surface reference friction related coefficient value.

The controller 9 may also store and compare the power or friction coefficient values over a predetermined amount of time, and use lowest values for wet reference, and highest values for dry reference.

Furthermore, the invention can be used to determine the weariness state of the wiper blades 5. Detecting the weariness state of the blades 5 allows to further reduce power consumption in that worn out blades have more important friction coefficients, in particular on dry windshield surface S, leading to increased power consumption.

Figure 5:
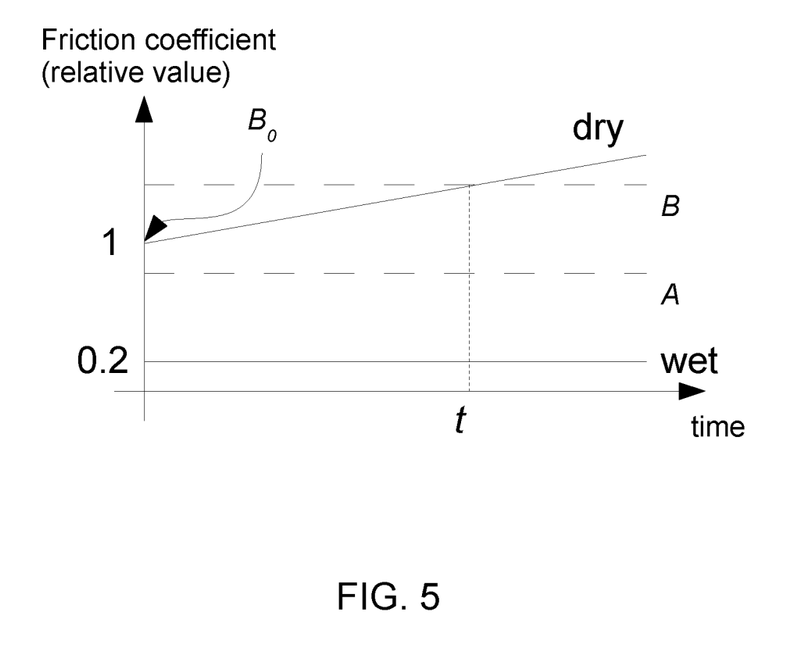
FIG. 5 is a graph representing the relative friction coefficient of a wiper blade over time.

FIG. 5 represents the friction coefficient of the blades 5 over life time. The friction coefficient is pictured in relative value, the base being the friction coefficient $B_0$ of new blades 5 on dry windshield surface S.

Experience shows that the coefficient value on wet surface is relatively independent from the weariness state of the blades 5, and remains at a value around 0.2 times the base value (factor five).

The friction on dry surface increases with weariness of blades 5. Therefore, a second threshold friction related coefficient value B can be set, above which the blades 5 are considered worn out. Said threshold value B can be a memorized value chosen according to nominal friction coefficient values on dry surface S.

On FIG. 5, the threshold value A, used to detect wetness state of surface S, and B, used to detect weariness of the blades 5 are represented by dotted lines.

B is above 1, and is reached at instant t. Upon detection of worn out state of the blades 5, an indicator can be lit on the dashboard to invite the user to proceed to a blade 5 renewing.

Said second threshold B value can also be determined during a calibration. During the second threshold value calibration, the controller 9 will run a predetermined number of wiping cycles on the dry windshield surface S at initiation of the vehicle electronics or after changing the blades 5.

Alternatively, the controller 9 can compare over time the highest registered friction coefficient or power values, and detect a rise in said maximum values.

By adapting the wiping speed W to the surrounding conditions, this method allows to reduce the power consumption of the wiping unit, since the risk of forgetting the wipers on a running position after it stopped raining is suppressed.

The method relies on a measure that implies the whole part of the windshield surface S that is wiped during a cycle, which is more reliable than the usual rain sensors 13, therefore, the methods to control power consumption using the wetness state determination according to the invention complement such rain sensors 13.

By reducing the probability of having the blades 5 wiping the dry surface S where the friction is more important, the method allows to enlarge the average lifespan of the blades 5.

Moreover, the method allows to estimate the state of weariness of said blades 5, inviting the user to change the blades 5 before they become unreliable or are worn out to a point that they lead to important added friction and thus power consumption.

The invention claimed is:

1. A method to detect the wetness state of a vehicle windshield surface comprising a windshield wiper unit, the windshield wiper unit comprising:
    wiper blades configured to wipe the vehicle windshield surface when set in motion,
    at least one motor configured to set the wiper blades in motion, and
    a controller, configured to control the at least one motor, the method comprising:
    measuring, by the controller, the power consumption of the at least one motor at a first time;
    determining, by the controller, the wiping speed of the wiper blades at the first time;
    using the measured power consumption at the first time and determined wiping speed at the first time to deduce, by the controller, a friction related coefficient of the vehicle windshield surface at the first time;
    making a first comparison, by the controller, of the deduced value at the first time to at least one predetermined value in order to determine the wetness state of the vehicle windshield surface at the first time;
    making a first determination, by the controller, that the vehicle windshield surface is dry based on the first comparison;
    stopping, by the controller, the motion of the wiper blades in response to the first determination;
    receiving, by the controller, a stop instruction that triggers a stop of motion of the wiper blades;
    measuring, by the controller, the power consumption of the at least one motor at a second time;
    determining, by the controller, the wiping speed of the wiper blades at the second time;
    using the measured power consumption at the second time and determined wiping speed at the second time to deduce, by the controller, a friction related coefficient of the vehicle windshield surface at the second time;
    making a second determination, by the controller, that the vehicle windshield surface is wet based on the first comparison; and
    maintaining, by the controller, the motion of the wiper blades in response to the second determination.

2. The method according to claim 1, wherein the controller stores and compares the friction related coefficient values over a predetermined amount of time, and uses lowest friction related coefficient values for wet state reference values, and highest friction related coefficient values for dry state reference values.

3. The method according to claim 1, the controller being connected to a windshield washing unit, wherein the predetermined value is determined using a calibration, the calibration comprising the steps:
    wetting the vehicle windshield surface by activating the windshield washing unit,
    measuring the power consumption of the at least one motor,
    determining the wiping speed of the wiper blades,
    using the measured power consumption and wiping speed to deduce a reference friction related coefficient of the wet vehicle windshield surface,
    setting the predetermined value to at least 150% of said wet vehicle windshield surface reference friction related coefficient value.

4. The method to claim 1, wherein detecting the wetness state and maintaining the wiping motion are repeated in a loop until detected wetness state is dry, the controller then stopping motion of blades.

5. A method to detect the weariness state of wiper blades of a vehicle windshield wiper unit, the windshield wiper unit comprising:
    at least one motor configured to set the wiper blades in motion,
    a controller, configured to control the at least one motor, wherein the method comprises:
        determining the wetness state of the vehicle windshield surface using the method according to claim 1;
        using the measured power consumption and determined wiping speed to deduce a friction related coefficient of the vehicle windshield surface;
        if the vehicle windshield surface is dry, comparing the deduced friction related coefficient value on dry windshield surface to at least one second predetermined value in order to determine the weariness state of wiper blades of the vehicle windshield wiper unit.

6. The method according to claim 5, wherein the controller compares over time the highest registered friction related coefficient values, and detects a rise in said maximum values in order to determine the weariness state of wiper blades of the vehicle windshield wiper unit.

7. The method according to claim 5, wherein the second predetermined value is determined using a calibration, the calibration comprising the steps:
    measuring the power consumption of the at least one motor on a dry windshield surface,
    determining the wiping speed of the wiper blades on the dry windshield surface,
    using the measured power consumption and determined wiping speed to deduce a reference friction related coefficient of the dry windshield surface, and
    using said reference dry windshield surface friction related coefficient to determine the second predetermined value.

8. A windshield wiper unit comprising:
    wiper blades configured to wipe a windshield surface when set in motion;
    at least one motor configured to set the wiper blades in motion; and
    a controller configured to control the at least one motor, wherein the controller comprises:
    means to measure a power consumption of the at least one motor, and means to determine a wiping speed of the wiper blades, the controller being configured to:
measure the power consumption at a first time and determine the wiping speed at the first time to deduce a friction related coefficient of the windshield surface at the first time,
make a first comparison of the deduced value at the first time to at least one predetermined value in order to determine the wetness state of the windshield surface at the first time,
make a first determination that the windshield surface is dry based on the first comparison;
stop the motion of the wiper blades in response to the first determination,
receive a stop instruction that triggers a stop of motion of the wiper blades,
measure the power consumption at a second time and determine the wiping speed at the second time to deduce a friction related coefficient of the windshield surface at the second time,
make a second comparison of the deduced value at the second time to the at least one predetermined value in order to determine the wetness state of the windshield surface at the second time,
make a second determination that the windshield is wet based on the second comparison, and
maintain, by the controller, the motion of the wiper blades in response to the second determination.

9. A windshield wiper unit comprising:
wiper blades configured to wipe a windshield surface when set in motion;
at least one motor configured to set the wiper blades in motion; and
a controller, configured to control the at least one motor, wherein the controller comprises:
means to measure a power consumption of the at least one motor, and
means to determine a wiping speed of the wiper blades, the controller being configured to:
measure the power consumption of the at least one motor,
determine the wiping speed of the wiper blades,
use the measured power consumption and determined wiping speed to deduce a friction related coefficient of the windshield surface,
and
when the windshield surface is set, compare the deduced friction related coefficient value on a wet windshield surface to at least one first predetermined value in order to determine the weariness state of wiper blades of the vehicle windshield wiper unit,
when the windshield surface is dry, compare the deduced friction related coefficient value on a dry windshield surface to at least one second predetermined value in order to determine the weariness state of wiper blades of the vehicle windshield wiper unit.

* * * * *